United States Patent [19]

Sumner, Jr. et al.

[11] Patent Number: 5,231,218

[45] Date of Patent: Jul. 27, 1993

[54] ISOMERIZATION OF DIMETHYLCYCLOHEXANEDICARBOXYLATE

[75] Inventors: Charles E. Sumner, Jr., Kingsport, Tenn.; William E. Choate, Longview, Tex.

[73] Assignee: Eastman Kodak Company, Rochester, N.Y.

[21] Appl. No.: 965,307

[22] Filed: Oct. 23, 1992

[51] Int. Cl.$^5$ .............................................. C07C 69/74
[52] U.S. Cl. .................................................... 560/127
[58] Field of Search ......................................... 560/127

[56] References Cited

U.S. PATENT DOCUMENTS

T911,020 6/1973 Stanin .................................. 560/127
3,133,973 5/1964 Smith .................................. 560/127

OTHER PUBLICATIONS

H. J. Naumann & H. Schmidt, J. Prakt, Chem. 4 Reihe Band 29, p. 232 (1965).

G. S. Gurevich, S. Z. Levin and I. S. Diner Zuhr. Obsh. Khi 33, No. 6, p. 1863 (1963).

S. Z. Levin, V. E. Griz and L. E. Spivak, C. A. 68, 8360, Item 86871 (1968).

L. F. Fieser and Mary Fieser, Organic Chemistry, Third Edition (1956) p. 291, Rheinhold Pub. Corp., N.Y.

A. K. Roebuck and B. L. Evering, J.A.C.S. 75, p. 1631 (1953).

M. Hino and K. Arata, J. Chem. Soc., Chem. Commun., p. 1355 (1987).

*Primary Examiner*—Michael L. Shippen
*Attorney, Agent, or Firm*—Bernard J. Graves, Jr.; William P. Heath, Jr.

[57] ABSTRACT

Provided is a fixed bed heterogeneous catalyst that promotes the isomerization of cis/trans-DMCD to trans-DMCD in economical fashion with short reaction times and in high purity. The catalyst is preferably $H_3PO_4$ on a metal oxide, said metal oxide selected from a group consisting of $ZrO_2$, $TiO_2$, $Al_2O_3$, and $HfO_2$, or a tungsten-modified $ZrO_2$.

20 Claims, No Drawings

ISOMERIZATION OF DIMETHYLCYCLOHEXANEDICARBOXYLATE

FIELD OF THE INVENTION

This invention belongs to the field of organic chemistry. In particular, this invention relates to a process for isomerizing cis-dimethylcyclohexanediacarboxylate.

BACKGROUND OF THE INVENTION

Trans-dimethylcyclohexanedicarboxylate (trans-DMCD) is useful for the synthesis of polyesters having enhanced weatherability as well as other unique properties. DMCD is commercially produced as a mixture of cis and trans isomers from the hydrogenation of dimethylterephthalate, with the major isomer being the cis configuration. In order to obtain useful quantities of trans-DMCD, the mixture is treated with a catalyst to isomerize the mixture to the thermodynamic equilibrium of 65% trans and 35% cis.

It is known that this isomerization can be carried out with a homogeneous catalyst comprised of the half acid ester of DMCD as the catalyst. The disadvantages of this approach are that long reaction times (48 h) are generally required and the yield of trans-DMCD is typically low (i.e., 70%-80%)—thus providing economic drawbacks as well as the adverse consequences of large amounts of wasteful by-products.

Traditional methods of isomerization such as treatment of the ester with a strong base such as methoxide are not generally considered acceptable in a large scale industrial process because of the expense associated with separating the base from the product mixture.

SUMMARY OF THE INVENTION

This invention describes a fixed-bed heterogeneous catalyst comprised of certain metal oxides modified with acidity-enhancing agents which promote the isomerization of cis/trans-DMCD to trans-DMCD in economical fashion with short reaction times and in high purity.

DETAILED DESCRIPTION OF THE INVENTION

The present invention provides a process for preparing a mixture of cis/trans dimethylcyclohexanedicarboxylate, said mixture being at least 50% trans-, which comprises treating a predominantly cis mixture of cis/trans dimethylcyclohexanedicarboxylate with a catalyst system comprised of an acidity-enhancing agent, preferably a tungsten-modified metal oxide, or $H_3PO_4$ on a metal oxide. Preferably, said metal oxide is selected from a group consisting of $ZrO_2$, $TiO_2$, $AlO_2$, and $HfO_2$ at a reaction temperature of about 150° to about 300° C.

In the process of the present invention, the use of a fixed bed catalyst has several advantages over a homogeneous catalyst. One of the more striking advantages is the savings realized from the ease of isolation of the product via filtration or other means of physical separation. In this case, the advantage is magnified with higher yield and lower equipment costs. The catalyst is preferably a $ZrO_2$ or $Al_2O_3$ that has been modified with phosphoric acid or another agent, e.g., tungsten, that will enhance the acidity of the metal oxide. Preferably, the metal oxide is soaked in a phosphoric acid solution for a day, washed, and dried in a vacuum. The resulting catalyst can be used as is, or can be heat treated to temperatures as high as 400° C. An active catalyst can also be obtained by treating the metal oxide ($ZrO_2$) with ammonium metatungstate according to the procedure outlined by M. Hino and K. Arata, *J. Chem. Soc., Chem. Commun.*, 1259 (1987).

As a preferred embodiment of the present invention, there is provided a process for preparing equilibrium mixture (65% trans; 35% cis)-DMCD, which comprises treating a mixture of cis- (70%) and trans- (30%) DMCD over a fixed-bed catalyst comprised of phosphoric acid on $ZrO_2$ or phosphoric acid on $Al_2O_3$, at elevated temperatures, preferably at about 235° C. The isomerization can also be promoted by tungsten modified $ZrO_2$. The preferred catalyst is phosphoric acid on $ZrO_2$, because $ZrO_2$ is substantially unaffected by the presence of carboxylic acids in the reaction mixture. The temperature range can vary over a wide range. Although isomerization will take place at temperatures a low as 200° C., the rate is generally too slow to be of much practical use. The catalyst is very effective at temperatures above 240° C., but a mechanism to heat the reaction mixture that is more expensive than 600 pound steam is required. The upper temperature range is believed to be about 270°-300° C. Thus, the reaction temperature is preferably about 200°-300° C.

The space time rate at 235° of material isomerized to near equilibrium (63% trans) is on the order of 366 g/L•h. Similar results were obtained with phosphoric on $Al_2O_3$ except that the rate of isomerization was only 55% trans at a feed rate of 365 g/L•h. In both cases, the rate of isomerization was inhibited by the presence of methylhydrogen cyclohexanedicarboxylate (MHCD). In the case of phosphoric acid on $ZrO_2$, the activity was resumed when MHCD was removed from the feed. However, in the case of phosphoric on $Al_2O_3$, the activity could not be restored. Phoshoric acid on $TiO_2$ is also an active catalyst, but the rate of isomerization at 235° C. is too low to be of much practical use. An advantage is that $TiO_2$ is also resistant to carboxylic acids much like $ZrO_2$.

In a preferred embodiment of the present invention, the predominately cis-DMCD mixture is heated to the reaction temperature by pumping it at a known rate to a bed of quarz chips lying over the catalyst bed. Usually, the pump rate is between 300-400 grams per liter of catalyst per hour (g/L•h), but is dependent upon the activity of the catalyst and the efficiency of contact between liquid and catalyst. In most experiments, the feed rate is adjusted so that the product exiting the reactor is at equilibrium with respect to the amount of trans isomer. The temperature of the reaction zone can range from the freezing point of the DMCD mixture to 300° C., but little isomerization takes place in a reasonable amount of time below 200° C. Above 300° C., considerable fouling of the catalyst and the formation of tar occurs. The preferred range is from 230°-250° C.

The trans-DMCD produced by the method of the present invention can be isolated and purified by standard methods. For example, the product mixture can be cooled so that the trans isomer crystallizes. The solid product can be separated by the use of a centrifuge or filtration. The mother liquor generally contains about 70% cis-DMCD and can be recycled to the front end of the process. Very little (<1%) of the material is lost during the process. The only identifiable yield loss is attributed to water in the DMCD feed, which is converted to MHCD via hydrolysis.

EXPERIMENTAL SECTION

Example 1

A one inch diameter reactor tube was packed for each experiment as follows: a one inch layer of quartz chips was placed at the base of the reactor portion of the tube, the catalyst layer (usually 12 to 13 inches in length, 100 mL of the appropriate catalyst), and a 12 to 14 inch layer of quartz chips above the catalyst bed. The reactor tube was suspended vertically in a three zone furnace (each zone was controlled independently), emptied into a steam-jacketed flask, and was maintained under a 50 mL/min nitrogen gas flow. DMCD feed was supplied to the reactor by a variable rate pump. Further, the portion of the tube exposed below the furnace and above the receiving flask was wrapped with heat tape to prevent the tube from becoming plugged with solid trans-DMCD.

Phosphoric Acid on Zirconia $H_3PO_4ZrO_2$ Catalyst

The phosphoric acid on zirconia catalyst was packed as stated above. The feed rate of DMCD (70% cis; 30% trans) was 0.61 g/min and the temperature of the catalyst bed was maintained at 235° C. The maximum MHCD content was 7.0 wt % for the first 3380 minutes of the run, during which time the product mixture was 57% trans. The MHCD content of the feed was reduced to around 1.5% for the remainder of the run, and the amount of trans in the mixture rose to 62%. The experiment was continued for a total time of 19440 minutes. No by-products were detected, while the amount of trans product remained at 62% and the mass balance was 99%.

Example 3

The procedure outlined in example 1 was followed. The catalyst was composed of $H_3PO_4/Al_2O_3$. The composition of the product was 52% trans over a 3280 minute period. The amount of MHCD in the feed was increased to 5%, which caused the amount of trans in the product to drop to 42%. This composition remained constant for an additional 2780 minutes (total time of 6060 minutes) until the experiment was discontinued.

Examples 4-8

The examples shown in the table below illustrate the effect of reactor temperature on the conversion to trans isomer and the purity of the DMCD product. The feed rates are listed in terms of gram DMCD per liter of catalyst per hour. The feed rates in these examples were varied in order to show the effectiveness of the catalyst as well as the temperature range.

TABLE 1

The Effect of Reactor Temperature on Performance of the $H_3PO_4/ZrO_2$ Catalyst

| Example No. | Temp. (C.) | Feed Rate g/L cat. | trans % | MHCD wt. % | DMCD wt. % |
|---|---|---|---|---|---|
| 4 | 252 | 1218 | 57 | 1.7 | 100.4 |
| 5 | 261 | 1218 | 66.6 | 1.1 | 101.6 |
| 6 | 290 | 2880 | 57.5 | 2.5 | 83.9 |
| 7 | 301 | 1506 | 63.5 | 3.6 | 93.5 |
| 8 | 312 | 2880 | 61.3 | 4.9 | 87.2 |

Example 9 Preparation of $H_3PO_4/ZrO_2$

A 1.0 L reaction vessel was charged with 0.2 L of pelletized $ZrO_2$. The pressure inside the vessel was reduced to 76 torr, and 0.3 L of 20% $H_3PO_4$ was aspirated into the vessel. (The concentration of $H_3PO_4$ can range from about 20% to 50%.) The pressure inside the vessel was then adjusted to atmospheric and the resulting mixture warmed to 75° C. for 24 hours. (The temperature for this step can range from about 70° C. to about 100° C.) The liquid was then drained from the reaction mixture and the resulting catalyst rinsed with 0.6 L of water. The title catalyst was then dried for 24 hours at 70° C. under a reduced pressure of 250 Torr.

Example 10—Isomerization of DMCD with a $ZrO_2$ Modified with Tungsten

The procedure outlined in Example 1 was followed except that the catalyst was composed of $ZrO_2$ that had been modified with tungsten according to the method of Hino and Arata. DMCD (70% cis isomer) was fed to the catalyst at a rate of 390 g/L•h at a temperature of 240° C. for 315 min. The product was 90% DMCD composed of 60% trans isomer, and 8% the hydrolysis product, MHCD. The feed rate was increased to 486 g/L•h for 60 min. The product was 98% DMCD containing 47% trans isomer, and 4% MHCD. Finally, the feed rate was increased to 594 g/L•h for 75 min. The product at these conditions was 99% DMCD containing 42% trans isomer, and 3% MHCD.

I claim:

1. A process for preparing a mixture of cis/trans dimethylcyclohexanedicarboxylate, which is at least 50% trans-, which comprises contacting at a reaction temperature of about 150° to about 300° C., a predominantly cis mixture of cis/trans dimethylcyclohexanedicarboxylate with a catalyst system comprised of a metal oxide which has been treated with $H_3PO_4$, wherein the metal oxide is selected from a group consisting of $ZrO_2$, $TiO_2$, $Al_2O_3$, and $HfO_2$, or a catalyst system comprised of a metal oxide selected from a group consisting of $ZrO_2$, $TiO_2$, $Al_2O_3$, and $HfO_2$, which has been treated with ammonium metatungstate.

2. The process of claim 1, wherein the reaction temperature is about 220° C. to 265° C.

3. The process of claim 1, wherein the metal oxide is $Al_2O_3$.

4. The process of claim 1, wherein the metal oxide is $ZrO_2$.

5. The process of claim 1, wherein the metal oxide is $TiO_2$.

6. The process of claim 1, wherein the metal oxide is $HfO_2$.

7. The process of claim 1, wherein the catalyst system is comprised of a metal oxide which has been treated with ammonium metatungstate.

8. The process of claim 7, wherein the metal oxide is $ZrO_2$.

9. The process of claim 10, wherein the reaction temperature is about 220° C. to 265° C.

10. A process for preparing a substantially thermodynamic equilibrium mixture of cis/trans dimethylcyclohexanedicarboxylate, which is approximately 65% trans-, which comprises treating a predominantly cis mixture of cis/trans dimethylcyclohexanedicarboxylate at a reaction temperature of about 150° to about 300° C., with a catalyst system comprised of a metal oxide which has been treated with $H_3PO_4$, wherein the metal oxide is selected from a group consisting of $ZrO_2$, $TiO_2$, $Al_2O_3$, and $HfO_2$, or a catalyst system comprised of a metal oxide selected from a group consisting of $ZrO_2$, $TiO_2$, Al$_2$O$_3$, and HfO$_2$, which has been treated with ammonium metatungstate.

11. The process of claim 10, wherein the reaction temperature is about 220° C. to 265° C.

12. The process of claim 10, wherein the metal oxide is Al$_2$O$_3$.

13. The process of claim 10, wherein the metal oxide is ZrO$_2$.

14. The process of claim 10, wherein the metal oxide is TiO$_2$.

15. The process of claim 10, wherein the metal oxide is HfO$_2$.

16. The process of claim 10, wherein the catalyst system is zirconium phosphate.

17. The process of claim 12, wherein the catalyst system is comprised of a metal oxide which has been treated with ammonium metatungstate.

18. The process of claim 17, wherein the metal oxide is ZrO$_2$.

19. The process of claim 18, wherein the reaction temperature is about 220° C. to 265° C.

20. A process for preparing a mixture of cis/trans dimethylcyclohexanedicarboxylate, which is at least 50% trans-, which comprises contacting a predominantly cis mixture of cis/trans dimethylcyclohexanedicarboxylate with a catalyst system comprised of zirconium phosphate, at a reaction temperature of about 150° to about 300° C.

* * * * *